United States Patent
Gu et al.

(10) Patent No.: US 11,850,285 B2
(45) Date of Patent: Dec. 26, 2023

(54) INSULIN-RESPONSIVE GLUCAGON DELIVERY PATCH

(71) Applicant: North Carolina State University, Raleigh, NC (US)

(72) Inventors: Zhen Gu, Apex, NC (US); Jicheng Yu, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 848 days.

(21) Appl. No.: 16/492,009

(22) PCT Filed: Mar. 7, 2018

(86) PCT No.: PCT/US2018/021336
§ 371 (c)(1),
(2) Date: Sep. 6, 2019

(87) PCT Pub. No.: WO2018/165294
PCT Pub. Date: Sep. 13, 2018

(65) Prior Publication Data
US 2021/0128738 A1    May 6, 2021

Related U.S. Application Data

(60) Provisional application No. 62/467,996, filed on Mar. 7, 2017.

(51) Int. Cl.
*A61K 47/64* (2017.01)
*A61K 47/61* (2017.01)
(Continued)

(52) U.S. Cl.
CPC .......... *A61K 47/645* (2017.08); *A61K 9/0021* (2013.01); *A61K 38/26* (2013.01);
(Continued)

(58) Field of Classification Search
CPC .... A61K 47/645; A61K 9/0021; A61K 38/26; A61K 38/28; A61K 47/32; A61K 47/56;
(Continued)

(56) References Cited

U.S. PATENT DOCUMENTS

| 7,329,742 B2 | 2/2008 | Doyle et al. |
| 2007/0099820 A1 | 5/2007 | Lancaster et al. |

(Continued)

FOREIGN PATENT DOCUMENTS

| CN | 101584867 A | 11/2009 |
| JP | 2016-047388 A | 4/2016 |
| WO | WO 2019/200081 A1 | 10/2019 |

OTHER PUBLICATIONS

Castle et al., "Novel Use of Glucagon in a Closed-Loop System for Prevention of Hypoglycemia in Type 1 Diabetes." Diabetes Care, vol. 33, pp. 1282-1287 (2010).

(Continued)

*Primary Examiner* — David Browe
(74) *Attorney, Agent, or Firm* — Jenkins, Taylor & Hunt, P.A.

(57) ABSTRACT

A composition comprising an insulin-polymer conjugate and an insulin aptamer-glucagon conjugate is described. Depending upon the amount of insulin in the environment surrounding the composition, the insulin aptamer of the insulin aptamer-glucagon conjugate can bind to insulin in the insulin-polymer conjugate to form a non-covalent conjugate. When the amount of insulin in the surrounding environment rises, the insulin aptamer-glucagon conjugate can be released. Thus, the composition can be used to deliver glucagon in an insulin responsive manner. The composition can be loaded into microneedles, for example, to prepare (Continued)

microneedle arrays for skin patches. Methods of delivering glucagon to a subject are also described.

29 Claims, 6 Drawing Sheets

Specification includes a Sequence Listing.

(51) Int. Cl.

| | |
|---|---|
| *A61K 47/69* | (2017.01) |
| *A61K 47/56* | (2017.01) |
| *A61P 3/10* | (2006.01) |
| *A61K 9/00* | (2006.01) |
| *A61K 38/26* | (2006.01) |
| *A61K 38/28* | (2006.01) |
| *A61K 47/32* | (2006.01) |
| *A61M 37/00* | (2006.01) |
| *B29C 39/02* | (2006.01) |
| *B29C 39/12* | (2006.01) |
| *C12N 15/115* | (2010.01) |
| *B29K 105/00* | (2006.01) |
| *B29L 31/00* | (2006.01) |

(52) U.S. Cl.
CPC ............. *A61K 38/28* (2013.01); *A61K 47/32* (2013.01); *A61K 47/56* (2017.08); *A61K 47/61* (2017.08); *A61K 47/6903* (2017.08); *A61M 37/0015* (2013.01); *A61P 3/10* (2018.01); *B29C 39/026* (2013.01); *B29C 39/123* (2013.01); *C12N 15/115* (2013.01); *A61M 2037/0023* (2013.01); *A61M 2037/0053* (2013.01); *A61M 2037/0061* (2013.01); *B29K 2105/0035* (2013.01); *B29K 2995/006* (2013.01); *B29K 2995/0092* (2013.01); *B29L 2031/756* (2013.01); *B29L 2031/7544* (2013.01); *C12N 2310/16* (2013.01)

(58) Field of Classification Search
CPC ............. A61K 47/61; A61K 47/6903; A61M 37/0015; A61M 2037/0023; A61M 2037/0053; A61M 2037/0061; A61P 3/10; B29C 39/026; B29C 39/123; C12N 15/115; C12N 2310/16; B29K 2105/0035; B29K 2995/006; B29K 2995/0092; B29L 2031/7544; B29L 2031/756
See application file for complete search history.

(56) References Cited

U.S. PATENT DOCUMENTS

| | | |
|---|---|---|
| 2011/0281939 A1 | 11/2011 | Zion et al. |
| 2012/0114558 A1 | 5/2012 | Stojanovic et al. |
| 2017/0080098 A1 | 5/2017 | Gu et al. |
| 2018/0110841 A1 | 4/2018 | Gu et al. |
| 2020/0330562 A1 | 10/2020 | Gu et al. |
| 2020/0360269 A1 | 11/2020 | Gu et al. |
| 2021/0161968 A1 | 6/2021 | Gu et al. |
| 2022/0160841 A1 | 5/2022 | Gu et al. |

OTHER PUBLICATIONS

Diabetes Control and Complications Trial Research Group, "The Effect of Intensive Treatment of Diabetes on the Development and Progression of Long-Term Complications in Insulin-Dependent Diabetes Mellitus." N. Engl. J. Med., vol. 329, pp. 977-986 (1993).
International Preliminary Report on Patentability Corresponding to International Application No. PCT/US 2018/021336 dated Sep. 19, 2019.
International Search Report and Written Opinion of the International Searching Authority Corresponding to International Application No. PCT/US 2018/021336 dated Jun. 12, 2018.
Jiang et al., "Gel-Liposome-mediated Co-Delivery of Anticancer Membrane-Associated Proteins and Small-Molecule Drugs for Enhanced Therapeutic Efficacy." Adv. Funct. Mat., vol. 24(16), pp. 2295-2304 (2014).
Jiang et al., "Glucagon and regulation of glucose metabolism." Am. J. Physiol. Endocrinol. Metab., vol. 284, pp. E671-E678 (2003).
Kogan et al., "Hyaluronic acid: a natural biopolymer with a broad range of biomedical and industrial applications." Biotechnol. Lett., vol. 29, pp. 17-25 (2007).
Mo et al., "Emerging micro- and nanotechnology based synthetic approaches for insulin delivery." Chem. Soc. Rev., vol. 43, pp. 3595-3629 (2014).
Nathan, "Intensive diabetes treatment and cardiovascular disease in patients with type 1 diabetes." N. Engl. J. Med., vol. 353, pp. 2643-2653 (2005).
Non-Final Office Action Corresponding to U.S. Appl. No. 16/492,009 dated May 12, 2022.
Ohkubo et al., "Intensive insulin therapy prevents the progression of diabetic microvascular complications in Japanese patients with non-insulin-dependent diabetes mellitus: a randomized prospective 6-year study." Diabetes Res. Clin. Pract., vol. 28, pp. 103-117 (1995).
Owens et al., "Insulins today and beyond." Lancet, vol. 358, pp. 739-746 (2001).
Pickup et al., "Nanomedicine and its potential in diabetes research and practice." Diabetes-Metab. Res. Rev., vol. 24, pp. 604-610 (2008).
Prausnitz et al., "Transdermal drug delivery." Nat. Biotechnol., vol. 26, pp. 1261-1268 (2008).
Prausnitz, "Microneedles for transdermal drug delivery." Adv. Drug Deliv. Rev., vol. 56, pp. 581-587 (2004).
Pu et al., "Insulin-binding aptamer-conjugated graphene oxide for insulin detection." Analyst, vol. 136, pp. 4138-4140 (2011).
Ravaine et al., "Chemically controlled closed-loop insulin delivery." J. Control. Release, vol. 132, pp. 2-11 (2008).
Russell et al., "Outpatient Glycemic Control with a Bionic Pancreas in Type 1 Diabetes." N. Engl. J. Med., vol. 371, pp. 313-325 (2014).
Stumvoll et al., "Type 2 diabetes: principles of pathogenesis and therapy." Lancet, vol. 365, pp. 1333-1346 (2005).
Tabak et al., "Prediabetes: a high-risk state for diabetes development." Lancet, vol. 379, pp. 2279-2290 (2012).
Veiseh et al., "Managing diabetes with nanomedicine: challenges and opportunities." Nat. Rev. Drug Discov., vol. 14, pp. 45-57 (2015).
Yu et al., "Insulin-responsive glucagon delivery for prevention of hypoglycemia." Small, vol. 13(19), pp. 1-5 (2017).
Yu et al., "Microneedle-array patches loaded with hypoxia-sensitive vesicles provide fast glucose-responsive insulin delivery." Proc. Natl. Acad. Sci. USA, vol. 112, pp. 8260-8265 (2015).

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: synthetic

```
<400> SEQUENCE: 1
ggtggtgggg ggggttggta gggtgtcttc                                30

<210> SEQ ID NO 2
<211> LENGTH: 28
<212> TYPE: DNA
<213> ORGANISM: Artificial sequence
<220> FEATURE:
<223> OTHER INFORMATION: synthetic

<400> SEQUENCE: 2 acagggtgt ggggacaggg gtgtgggg                                   28

<210> SEQ ID NO 3
<211> LENGTH: 29
<212> TYPE: PRT
<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Lys Met Asn Thr
            20                  25

<210> SEQ ID NO 4
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: The guanine at position 1 is an amino-modified
      guanine

<400> SEQUENCE: 4
ggtggtgggg ggggttggta gggtctcttc                                30
```

INSULIN-RESPONSIVE GLUCAGON DELIVERY PATCH

RELATED APPLICATIONS

This application claims priority to and the benefit of U.S. Provisional Patent Application Ser. No. 62/467,996, filed Mar. 7, 2017; the disclosure of which is incorporated herein by reference in its entirety.

TECHNICAL FIELD

The presently disclosed subject matter relates to systems and compositions, including non-covalent conjugate compositions, microneedles, and microneedle arrays, for the insulin-responsive delivery of glucagon. The presently disclosed subject matter further relates to methods of preparing the compositions and to methods of delivering glucagon to a subject in need thereof.

Abbreviations

° C.=degrees Celsius
%=percentage
μL=microliter
μm=micrometer or micron
Apt=aptamer
BGL=blood glucose level
cm=centimeter
DI=deionized
dL=deciliter
ELISA=enzyme linked immunosorbent
FESEM=field-emission scanning electron microscope
FITC=fluorescein isothiocyante
Glu=glucagon
h=hour
HA=hyaluronic acid
IU=international units
KCl=potassium chloride
$KH_2PO_4$=monopotassium phosphate
MBA=N,N'-methylene bisacrylamide
mg=milligram
m-HA=acrylate-modified hyaluoric acid
min=minutes
mL=milliliter
mm=millimeter
mM=millimolar
Mn=number-average molecular weight
MN=microneedle
N=Newton
NaCl=sodium chloride
$Na_2HPO_4$=disodium phosphate
nm=nanometer
NMR=nuclear magnetic resonance
$O_2$=oxygen
PBS=phosphate buffered saline
PEG=poly(ethylene glycol)
s=seconds
SEM=scanning electron microscope
Ser=serine
STZ=streptozotocin
UV=ultraviolet

BACKGROUND

Diabetes mellitus is a group of metabolic diseases characterized by the accumulation of glucose in the blood. See Pickup et al., Diabetes-Metabolism Research and Reviews, 24, 604-610 (2008); and Stumvoll et al., Lancet, 365, 1333-1346 (2005). As of 2014, 387 million people suffered from diabetes worldwide, and the number is estimated to be 592 million by 2035. See Mo et al., Chemical Society Reviews, 43, 3595-3629 (2014); and Tabák et al., Lancet, 379, 2279-2290 (2012). Insulin replacement is generally considered essential for type 1 and advanced type 2 diabetic patients. See Owens et al., Lancet, 358, 739 (2001); and Mo et al., Chemical Society Reviews, 43, 3595 (2014). Intensive insulin therapy of type 1 diabetes is associated with improved glycemic control and decreased risk of long-term complications. See Control et al., N. Engl. J. Med., 329, 977 (1993); and Nathan, N. Engl. J. Med., 353, 2643 (2005). But, frequent insulin dosing and boluses, either through injection or through subcutaneous insulin infusion, can also lead to an increasing risk of hypoglycemia, or dangerously low levels of glucose in the blood. Episodes of hypoglycemia are characterized by behavioral and cognitive disturbance, and if untreated, can progress to seizure, coma, and even death. See Ohkubo et al., Diabetes Research and Clinical Practice, 28, 103 (1995). Despite treatment advances in electronic/mechanical insulin delivery devices and in chemical approaches to insulin delivery, hypoglycemia still remains a concern, even in a closed-loop insulin delivery system. See Veiseh et al., Nature Reviews Drug Discovery, 14, 45 (2015).

Glucagon, a peptide hormone produced by the alpha cells of the pancreas, works to counteract the effect of insulin and raises blood glucose levels (BGL). The pancreas releases glucagon when BGL are low, which acts in the liver to promote conversion of stored glycogen into glucose that is released into the bloodstream. See Jiana et al., American Journal of Physiology-Endocrinology and Metabolism, 284, E671 (2003); and Castle et al., Diabetes Care, 33, 1282 (2010). Thus, glucagon can be effective for the prevention and treatment of hypoglycemia, and several dual hormone (insulin and glucagon) infusion pumps with continuous glucose monitoring systems have been developed to improve blood glucose control. See Russell et al., N. Engl. J. Med., 371, 313 (2014); and Ravaine et al., Journal of Controlled Release, 132, 2 (2008). However, the lag in glucose feedback and biofouling still limit the further clinical applications of these electronic/mechanical devices. See Mo et al., Chemical Society Reviews, 43, 3595 (2014); and Pu et al., Analyst, 136, 4138 (2011).

Accordingly, there is still a need for additional glucagon delivery systems and related compositions, particularly for "closed-loop" delivery systems that can deliver glucagon to a subject rapidly in response to changes in blood insulin levels and/or with little to no pain.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

In some embodiments, the presently disclosed subject matter provides a composition comprising: (a) a polymer-insulin conjugate comprising a polymer covalently conjugated to insulin or to a bioactive derivative thereof; and (b) an insulin aptamer-glucagon conjugate comprising an insulin aptamer covalently conjugated to glucagon or to a bioactive derivative thereof; wherein the insulin aptamer can selectively bind to the insulin or bioactive derivative thereof, thereby forming a non-covalent conjugate between (a) and (b).

In some embodiments, the polymer is biodegradable. In some embodiments, the polymer is a hydrophilic polymer, optionally wherein the hydrophilic polymer is a polyamino acid, such as polyglutamic acid, a synthetic block copolymer, or a polysaccharide, further optionally wherein the polysaccharide is a glucosaminoglycan. In some embodiments, the polymer is hyaluronic acid or a derivatized hyaluronic acid, optionally wherein the polymer is a methacrylated hyaluronic acid.

In some embodiments, the polymer and the insulin or bioactive derivative thereof are covalently conjugated via an amide linkage. In some embodiments, the insulin is human recombinant insulin.

In some embodiments, the insulin aptamer is an oligonucleotide, optionally wherein the oligonucleotide comprises the sequence of SEQ ID NO: 1 or SEQ ID NO: 4. In some embodiments, the glucagon is a thiolated glucagon and the glucagon and the insulin aptamer are covalently conjugated via a linker, optionally wherein the linker is sulfosuccinimidyl-4-(N-maleimidomethyl)-cyclohexane-1-carboxylate (Sulfo-SMCC).

In some embodiments, the composition is cross-linked with a crosslinker to form a hydrogel matrix, optionally wherein the crosslinker is N,N'-methylenebisacrylamide.

In some embodiments, the presently disclosed subject matter provides a pharmaceutical composition comprising a composition comprising (a) a polymer-insulin conjugate and (b) an insulin aptamer-glucagon conjugate; and a pharmaceutically acceptable carrier.

In some embodiments, the presently disclosed subject matter provides a microneedle array comprising a composition comprising (a) a polymer-insulin conjugate and (b) an insulin aptamer-glucagon conjugate; optionally wherein said microneedle array comprises a plurality of microneedles, wherein each of said plurality of microneedles has a length of between about 20 and about 1000 microns, further optionally wherein each of the plurality of microneedles has a length of about 600 microns. In some embodiments, the microneedle array is provided as part of a skin patch, optionally wherein said skin patch comprises one or more backing layers and/or skin-compatible adhesives.

In some embodiments, the presently disclosed subject matter provides a closed-loop glucagon delivery system comprising a microneedle array, wherein said microneedle array comprises a composition comprising (a) a polymer-insulin conjugate and (b) an insulin aptamer-glucagon conjugate.

In some embodiments, the presently disclosed subject matter provides a method of delivering glucagon or a bioactive derivative thereof to a subject in need thereof, the method comprising providing a microneedle array comprising a composition comprising (a) a polymer-insulin conjugate and (b) an insulin aptamer-glucagon conjugate; and applying said array to a skin surface of said subject. In some embodiments, the delivery of the glucagon or the bioactive derivative thereof is at a rate corresponding to the insulin concentration coming into contact with the microneedle array.

In some embodiments, the subject is a mammal. In some embodiments, the subject is diabetic and/or is being treated for a disease or disorder with insulin replacement therapy, a sulfonylurea, or a meglitinide. In some embodiments, the subject is non-diabetic and suffers from hyperinsulinemic hypoglycemia, optionally wherein the subject has a disease or disorder selected from the group comprising congenital hyperinsulinism, an insulinoma, gastric dumping syndrome, autoimmune insulin syndrome, or reactive hypoglycemia.

In some embodiments, the presently disclosed subject matter provides a method of preparing a microneedle array for the insulin-responsive delivery of glucagon or a bioactive derivative thereof, the method comprising: (a) providing a mold comprising one or more microcavities, optionally wherein each of the one or more microcavities is approximately conical in shape and/or wherein the microcavities have a depth of between about 300 and about 900 micrometers; (b) filling at least a portion of the one or more microcavities of the mold with a first solution comprising: (i) a composition comprising an polymer-insulin conjugate and an insulin aptamer-glucagon conjugate; (ii) a crosslinking agent; and (iii) a photoinitiator; (c) drying the filled mold to remove water; (d) removing the mold to provide a microneedle array; and (e) exposing the microneedle array to UV radiation to provide a crosslinked microneedle array.

In some embodiments, the mold comprises silicone. In some embodiments, the method further comprises filling a portion of the mold with a second solution comprising a biocompatible polymer, optionally methacrylated hyaluronic acid, a crosslinking agent, and a photoinitiator.

Accordingly, it is an object of the presently disclosed subject matter to provide insulin-responsive compositions (e.g., hydrogels and/or microneedle arrays) for the delivery of glucagon, as well as methods of preparing and using said compositions.

An object of the presently disclosed subject matter having been stated hereinabove, and which is achieved in whole or in part by the presently disclosed subject matter, other objects will become evident as the description proceeds when taken in connection with the accompanying drawings and examples as best described herein below.

BRIEF DESCRIPTION OF THE SEQUENCE LISTING

Figure 1:
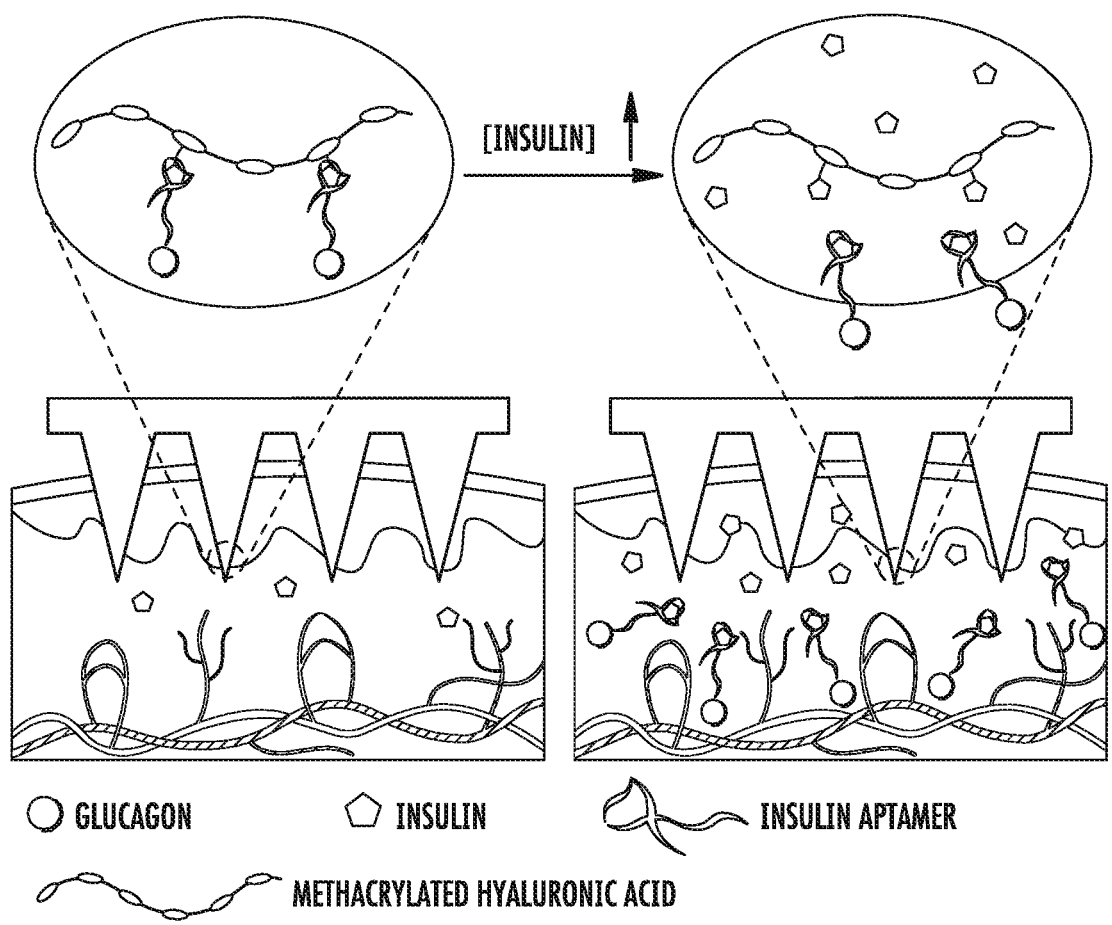
FIG. 1 is a schematic drawing of an insulin-responsive glucagon delivery system of the presently disclosed subject matter comprising a microneedle (MN)-array patch comprising an insulin-methacrylated hyaluronic acid conjugate and an insulin aptamer-glucagon conjugate. When interstitial fluid insulin levels are low (left), glucagon-insulin aptamer remains bound to the insulin conjugated to the methacrylated hyaluronic acid polymer in the patch. When interstitial fluid insulin levels rise (right), the glucagon-insulin aptamer is released from the patch. Glucagon is represented by circles and insulin by pentagons. The methacrylated hyaluronic acid is represented by a structure comprising ovals joined by single lines. The insulin aptamer is represented by a complex of three double lined structures that form a roughly triangular structure with two tails of differing length.

SEQ ID NO: 1 is an oligonucleotide sequence of an exemplary insulin binding aptamer of the presently disclosed subject matter.

SEQ ID NO: 2 is an oligonucleotide sequence of another exemplary insulin binding aptamer of the presently disclosed subject matter.

SEQ ID NO: 3 is a polypeptide sequence for human glucagon.

SEQ ID NO: 4 is an oligonucleotide sequence of an exemplary 5' amino-modified insulin binding aptamer of the presently disclosed subject matter.

DETAILED DESCRIPTION

The presently disclosed subject matter will now be described more fully hereinafter with reference to the accompanying Examples and Drawings, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which the presently described subject matter belongs. All publications, patent applications, patents, and other references mentioned herein are incorporated by reference in their entirety.

Throughout the specification and claims, a given chemical formula or name shall encompass all active optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a composition" or "a polymer" includes a plurality of such compositions or polymers, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter or length), weight, concentration, temperature, volume, or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, nitro, amino, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "aralkyl" refers to an -alkyl-aryl group, optionally wherein the alkyl and/or aryl group comprises one or more alkyl or aryl group substituents.

In some embodiments, the term "bivalent" refers to a group that can bond (e.g., covalently bond) or is bonded to two other groups, such as other alkyl, aralkyl, cycloalkyl, or aryl groups. Typically, two different sites on the bivalent group (e.g., two different atoms) can bond to groups on other molecules. For example, the bivalent group can be an alkylene group.

"Alkylene" can refer to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($-CH_2-$); ethylene ($-CH_2-CH_2-$); propylene ($-(CH_2)_3-$); cyclohexylene ($-C_6H_{10}-$); $-CH=CH-CH=CH-$; $-CH=CH-CH_2$; $-(CH_2)_q-N(R)-(CH_2)_r-$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($-O-CH_2-O-$); and ethylenedioxyl ($-O-(CH_2)_2-O-$). An alkylene group can have about 2 to about 3 carbon atoms and can further have 6-20 carbons.

"Arylene" refers to a bivalent aryl group.

The term "amino" refers to the $-NR'R''$ group, wherein R' and R'' are each independently selected from the group including H and substituted and unsubstituted alkyl, cycloalkyl, heterocycle, aralkyl, aryl, and heteroaryl. In some embodiments, the amino group is $-NH_2$, which can also be referred to as a "primary amine" group. "Aminoalkyl" and "aminoaryl" refer to the $-NR'R''$ group, wherein R' is as defined hereinabove for amino and R'' is substituted or unsubstituted alkyl or aryl, respectively.

The terms "carboxylate" and "carboxylic acid" can refer to the groups $-C(=O)O^-$ and $-C(=O)OH$, respectively. In some embodiments, "carboxylate" can refer to either the $-C(=O)O^-$ or $-C(=O)OH$ group.

The term "amide" refers to the $-C(=O)-NR-$ group, wherein R is H, alkyl, aralkyl or aryl.

The term "thiol" refers to the $-SH$ group.

The term "thioether" refers to a $R-S-R'$ group, wherein R and R' are each independently selected from the group including substituted and unsubstituted alkyl, cycloalkyl, heterocycle, aralkyl, aryl and heteroaryl.

The term "micro" (e.g., in "microneedle") as used herein refers to a structure having at least one region with a dimension of less than about 1,000 microns (μm). In some embodiments, the term "micro" refers to a structure having a dimension between about 1 micron and about 1,000 microns (e.g., about 1, 5, 10, 25, 50, 75, 100, 200, 300, 400, 500, 600, 700, 800, 900 or about 1,000 microns)

The terms "polymer" and "polymeric" refer to chemical structures that have repeating units (i.e., multiple copies of a given chemical substructure). As used herein, polymers can refer to groups having more than 10 repeating units and/or to groups wherein the repeating unit is other than methylene. Polymers can be formed from polymerizable monomers. A polymerizable monomer is a molecule that comprises one or more reactive moieties {e.g., siloxy ethers, hydroxyls, amines, vinylic groups (i.e., carbon-carbon double bonds), halides (i.e., Cl, Br, F, and I), carboxylic acids, esters, activated esters, and the like} that can react to form bonds with other molecules. Generally, each polymerizable monomer molecule can bond to two or more other molecules. In some cases, a polymerizable monomer will bond to only one other molecule, forming a terminus of the polymeric material. Some polymers contain biodegradable linkages, such as esters or amides, such that they can degrade overtime under biological conditions.

A "copolymer" refers to a polymer derived from more than one species of monomer.

As used herein, a "block copolymer" refers to a copolymer that comprises blocks (i.e., polymeric sub-sections of the whole copolymer) in a linear sequence. A "block" refers to a portion of a copolymer that has at least one feature that is not present in the adjacent portions of the macromolecule. Thus, a "block copolymer" can refer to a copolymer in which adjacent blocks are constitutionally different, i.e., each of these blocks comprises constitutional units derived from different characteristic species of monomer or with different composition or sequence distribution of constitutional units.

For example, a diblock copolymer of PEG and polyserine can be referred to as PEG-block-polyserine. Such a copolymer can also be referred to generically as an "AB block copolymer." Likewise, a triblock copolymer can be represented as "ABA." Other types of block polymers exist, such as multiblock copolymers of the $(AB)_n$ type, ABC block polymers comprising three different blocks, and star block polymers, which have a central point with three or more arms, each of which is in the form of a block copolymer, usually of the AB type.

"Biocompatible" as used herein, generally refers to a material and any metabolites or degradation products thereof that are generally non-toxic to the recipient and do not cause any significant adverse effects to the recipient.

"Biodegradable" as used herein, generally refers to a material that will degrade or erode under physiologic conditions to smaller units or chemical species that are capable of being metabolized, eliminated, or excreted by the subject. In some embodiments, the degradation time is a function of polymer composition and morphology. Suitable degradation times are from days to weeks. For example, in some embodiments, the polymer can degrade over a time period from seven days to 24 weeks, optionally seven days to twelve weeks, optionally from seven days to six weeks, or further optionally from seven days to three weeks.

The term "hydrophilic" can refer to a group that dissolves or preferentially dissolves in water and/or aqueous solutions.

The term "hydrophobic" refers to groups that do not significantly dissolve in water and/or aqueous solutions and/or which preferentially dissolve in fats and/or non-aqueous solutions.

The terms "conjugate" and "conjugated" can refer to compositions that comprise at least two different chemical moieties or molecules (e.g., small molecules, polymers, proteins, oligonucleotides, etc.) bonded to one another, such as via ionic, coordinative or covalent bonds. Typically, a "conjugate" refers to a situation where the two entities are bonded via a single bond or linkage. In some embodiments, the term "conjugate" refers to moieties or molecules that are covalently bonded to one another. In some embodiments, the conjugate can comprise two different chemical moieties associated with one another via intermolecular forces such as hydrogen bonding, London dispersion forces, van der Waals' interactions, etc.

The term "insulin" as used herein refers to insulin from a human or other mammal. In some embodiments, the term "insulin" refers to human insulin. In some embodiments, the term "insulin" refers to recombinant human insulin.

The term "glucagon" as used herein refers to glucagon from a human or from other mammals. In some embodiments, the term "glucagon" refers to human glucagon. In some embodiments, the term "glucagon" refers to recombinant human glucagon. In some embodiments, the term "glucagon" refers to a bioactive derivative of glucagon.

"Bioactive derivative" as used herein in reference to insulin or to glucagon refers to insulin (e.g., human insulin or another mammalian insulin) or glucagon in which one or more amino acid residues have been replaced by another amino acid residue or deleted, in which the A chain and/or the B chain of the insulin or the amino acid sequence of the glucagon has been extended by addition of one or more amino acid residues at the N-terminal or at the C-terminal, and/or in which the insulin or glucagon has been otherwise modified, such as by the addition of one or more chemical substituents. The derivative can function to replace endogenous insulin or endogenous glucagon and retains at least some of the biological activity of endogenous insulin or endogenous glucagon. In some embodiments, the bioactive derivative has essentially the same biological activity as endogenous insulin or endogenous glucagon, such as endogenous human insulin or endogenous human glucagon. Bioactive derivatives can have different pharmacokinetics than endogenous peptides or proteins. Dosages can be optimized based on the pharmacokinetics of the derivative relative to human insulin or human glucagon based on known pharmacokinetics by one of skill in the art.

The term "diabetes treatment agent" as used herein can refer to a therapeutic agent that treats diabetes or a complication thereof (such as, but not limited to, diabetic neuropathy, diabetic retinopathy, diabetic nephropathy, glaucoma, and diabetic ketoacidosis) or another glucose metabolism disorder that results in hyperglycemia. In some embodiments, the diabetes treatment agent is an insulin or a bioactive derivative thereof or a non-insulin-based treatment agent known in the art for use in the treatment of diabetes. Suitable non-insulin-based treatment agents for use in the treatment of diabetes include, but are not limited to, insulin sensitizers, DPP IV inhibitors, glucagon-like peptide 1 (GLP-1) and analogs thereof, insulin secretagogues, such as, but not limited to sulfonylureas, meglitinides, gastric inhibitory polypeptide (GIP), insulin receptor activators, biguanides, thiazolidinediones, alpha-glucosidase inhibitors, and the like. In some embodiments, the diabetes treatment agent is an insulin or a bioactive derivative.

The terms "bifunctional linker", "cross-linking reagent" or "cross-linking agent" refer to a compound that includes at least two reactive functional groups (or groups that can be deblocked or deprotected to provide reactive functional groups), which can be the same (i.e., in a homobifunctional linker) or different (in a heterobifunctional linker). In some embodiments, the cross-linking reagent is a heterobifunctional linker and the two reactive functional groups can have different chemical reactivity (e.g., the two reactive functional groups are reactive (e.g., form bonds, such as covalent bonds) with different types of functional groups on other molecules, or one of the two reactive functional groups tends to react more quickly with a particular functional group on another molecule than the other reactive functional group). Thus, the cross-linking reagent can be used to link (e.g., covalently bond) two other entities (e.g., molecules, polymers, proteins, nucleic acids, vesicles, liposomes, nanoparticles, microparticles, etc.) or to link two groups on the same entity (e.g., a polymer) to form a cross-linked composition. Generally, as used herein, the term "cross-linked" refers to a composition comprising multiple bonds or linkages between two entities or comprising multiple added bonds or linkages between groups on the same entity.

The term "hyperglycemia", as used herein, can refer to a condition in which an elevated amount of glucose circulates in the blood plasma of a subject relative to a healthy individual. Hyperglycemia can be diagnosed using methods known in the art, including measurement of fasting blood glucose levels.

The term "hypoglycemia", as used herein, can refer to a condition in which a reduced amount of glucose circulates in the blood plasma of a subject. The reduced level of glucose that can signify hypoglycemia can vary depending upon the age and health of a subject. For a diabetic adult, a blood glucose level of 70 mg/dL or less can be referred to as hypoglycemia. For a non-diabetic adult, a blood glucose level of 50 mg/dL or less can be referred to as hypoglycemia. Hypoglycemia can be diagnosed using methods known in the art, including via the use of a commercially available fingerstick blood glucose monitors, continuous blood glucose monitors, measuring venous blood glucose levels, etc. Symptoms of hypoglycemia include, but are not limited to, jitters, blurred vision, sweating, pallor, personality changes, headaches, weakness, hunger, sleepiness, nausea, dizziness, trouble concentrating, irregular heartbeat, confusion, seizures, and coma.

In some embodiments, the hypoglycemia can be related to an elevated level of insulin circulating in the blood, i.e., hyperinsulinemic hypoglycemia. In some embodiments, the hyperinsulinemic hypoglycemia can be the result of treatment of type 1 or type 2 diabetes with insulin replacement therapy (e.g., insulin injection) and/or with another diabetic treatment agent (e.g., a sulfonylurea or a meglitinide). Thus, in some embodiments, the hypoglycemia can be caused by an excess of injected insulin. In some embodiments, the hypoglycemia can be caused by an excess of endogenous insulin. In some embodiments, the hyperinsulinemic hypoglycemia can be caused by, for example, congenital hyperinsulinism, an insulinoma (e.g., an islet cell adenoma or carcinoma), gastric dumping syndrome, autoimmune insulin syndrome, reactive hypoglycemia, or noninsulinoma pancreatogeneous hypoglucemia. In some embodiments, the use of certain drugs, such as, but not limited to sulfonylureas, meglitinides, aspirin, pentamide, quinine, or disoperamide, can result in hypoglycemia. Hypoglycemia can be treated, for example with glucagon, recombinant glucagon (sold under the trade name GlucaGen), or diazoxide, a benzothiadiazine, sold under the trade names Proglycem and Hyperstat.

The term "aptamer", as used herein, refers to a peptide or oligonucleotide that can selectively bind to a particular target molecule. In some embodiments, the aptamer is a single-stranded nucleic acid (RNA, DNA, or modified form thereof) whose distinct nucleotide sequence determines the folding of the aptamer into a particular three-dimensional structure. Nucleic acid aptamers typically comprise a degenerate or random sequence flanked by fixed sequences onto which primers may bind for amplification. Modified DNA and/or RNA bases may be used or incorporated as desired, e.g., beta-D-Glucosyl-Hydroxymethyluracil. See, e.g., U.S. Pat. No. 7,329,742. The nucleic acids can include any combination of naturally-occurring nucleosides (A, G, C, T, U), and/or nucleoside or nucleotide analogs and/or derivatives as are well known in the art, including cytotoxic, synthetic, rare, non-natural bases or altered nucleotide bases. In addition, a modification can be incorporated to reduce exonucleolytic degradation. In some embodiments, the aptamer is an oligonucleotide consisting essentially of between about 5 and about 150 or between about 20 and about 150 nucleotides (e.g., between 20 and 120 nucleotides, between 25 and 100 nucleotides, or between about 30 and 50 nucleotides) that further comprises a reactive group (e.g., an amino group) that can be used to form a covalent attachment to a molecule of interest or to a chemical linker. In some embodiments, the aptamer comprises a 5' amino group.

Suitable aptamers that selectively bind a particular target molecule (e.g., a particular protein) can be selected in vitro through methods known in the art, such as SELEX (Systematic Evolution of Ligands by Exponential Enrichment). Nucleic acid aptamers have many advantages. Due to their oligonucleotide nature, nucleic acid aptamers possess a low immunogenicity and are highly resistant to stringent physico-chemical conditions (presence of urea, DMSO, highly acidic or basic pH values, use of organic solvents or high temperatures). In addition, they are highly selective.

As used herein, the term "insulin aptamer" refers to an aptamer that selectively binds insulin. In some embodiments, the insulin aptamer is a single stranded nucleic acid.

The terms "specific binding", "selectively bind" or "selectively binding" when used in reference to the interaction of an aptamer and a target molecule (e.g., insulin) mean that the aptamer binds to the target molecule without substantially binding to any other molecule that might be present in the same environment, sample, or mixture as the aptamer. Thus, an aptamer that selectively binds to insulin refers to an aptamer that binds to insulin (e.g., human insulin), but that has a reduced ability or no ability to bind to other proteins or molecules that might be present in a biological sample or environment. Thus, the aptamer has discrimination capacities between insulin and other biological molecules. In some embodiments, the term "selectively binds" refers to an aptamer that once bound to a particular target (e.g., insulin) will only disassociate from that target to bind to another molecule of the same target (i.e., another insulin molecule).

In some embodiments, the ability of the aptamer used to discriminate the target molecule (e.g., insulin) from other proteins and/or biological molecules is such that the aptamer has an affinity for the target molecule defined by a dissociation constant value ($K_d$), expressed in molar concentration, which is lower by at least one order of magnitude as compared to the dissociation constant value of said aptamer towards any other biological molecule that might be present in a sample with the target. In some embodiments, the aptamer binds to the target with an affinity characterized by a dissociation constant value (Kd) ranging from 1 pM to 10 μM, or ranging from 10 nM to 10 μM. In some embodiments, the affinity of the aptamer for the target protein is 10, 100, 250, 500, 1000, 5,000, or 10,000 times higher than the affinity of the aptamer for another molecule present in the same sample or environment.

II. General Considerations

The presently disclosed subject matter relates, in some embodiments, to compositions for the delivery of glucagon (or a bioactive derivative thereof) to a subject in need thereof, e.g., for the control of hypoglycemia, such as hypoglycemia resulting from treatment related to diabetes or hypoglycemia related to another condition that results in hyperinsulinemic hypoglycemia. The compositions could also be useful for delivering other drugs to treat hypoglycemia and/or the side effects thereof (e.g., by incorporating another drug into the composition in addition to or in place of the glucagon).

In some embodiments, according to an exemplary embodiment of the presently disclosed subject matter, the presently disclosed subject matter provides an insulin-responsive glucagon delivery system, which can be incorporated, for example, into a microneedle-based transdermal patch. The patch can be used, for instance, for prevention of hypoglycemic episodes during diabetes management. More particularly, in some embodiments, to provide insulin-responsiveness, an insulin aptamer comprising a single-stranded oligonucleotide with a secondary structure that can selectively bind to its target insulin is conjugated to glucagon. Insulin aptamers for insulin sensing have been previously described the art. See, e.g., Pu et al. Analyst, 136, 4138 (2011).

In a representative embodiment of the presently disclosed subject matter, an aptamer-glucagon conjugate (Apt-Glu) is further bound to insulin immobilized on a polymer carrier, methacrylated hyaluronic acid (m-HA), through the interaction between the insulin aptamer and the polymer-immobilized insulin. HA has high biocompatibility and biodegradability. See Kogan et al., Biotechnology Letters, 29, 17 (2007). However, any other suitable bio-compatible polymer can be used. In some embodiments, a crosslinked insulin-responsive glucagon conjugated polymer (i.e., an insulin-responsive glucagon conjugated HA (Glu-HA)) matrix can be formed via polymerization with crosslinkers and a photo-initiator using UV irradiation. See Jiang et al., Advanced Functional Materials, 24, 2295 (2014). In the presence of a high insulin concentration, glucagon can be rapidly released from the polymer matrix (e.g., the HA matrix) through the competitive binding between free insulin and the insulin immobilized on the polymer (i.e., the HA).

For a long-term, painless, and convenient treatment (see Prausnitz et al., Nature Biotechnology, 26, 1261 (2008); and Yu et al., PNAS, 112, 8260 (2015)), the insulin-responsive Glu-polymer (e.g., Glu-HA) matrix can be further integrated with a microneedle (MN)-array patch for transcutaneous administration. The MNs formed from the insulin-responsive Glu-polymer are able to release glucagon in response to elevated interstitial fluid insulin levels in vascular and lymph capillary networks, thereby preventing the risk of hypoglycemia. See FIG. 1. For example, in a representative embodiment described further hereinbelow, an insulin-triggered glucagon delivery system can provide prevention of hypoglycemia after injection of a high dose of insulin in a streptozotocin (STZ)-induced type 1 diabetic mouse model. Thus, the presently disclosed MN glucagon-delivery patches can be useful, for instance, in improving the health, as well as the quality of life, of type 1 and advanced type 2 diabetic patients by both facilitating insulin intensification with reduced risk of hypoglycemia and preventing morbidity and mortality from severe episodes of hypoglycemia. This aptamer-incorporated controlled release method can also be extended to engineer other closed-loop therapeutic delivery systems to treat a variety of other diseases.

Accordingly, in some embodiments, the presently disclosed subject matter provides a composition comprising: (a) a polymer-insulin conjugate comprising a polymer covalently conjugated to insulin or to a bioactive derivative thereof; and (b) an insulin aptamer-glucagon conjugate comprising an insulin aptamer covalently conjugated to glucagon or to a bioactive derivative thereof; wherein the insulin aptamer can selectively bind to the insulin or bioactive derivative thereof, thereby forming a non-covalent conjugate between (a) and (b).

Any suitable polymer can be used as part of the polymer-insulin conjugate. In some embodiments, the polymer is biocompatible and/or biodegradable. In some embodiments, the polymer is a hydrophilic polymer, such as, but not limited to a polyamino acid, such as polyglutamic acid; a synthetic block copolymer, or a polysaccharide, e.g., a glucosaminoglycan. In some embodiments, the polymer is hyaluronic acid or a derivatized hyaluronic acid. In some embodiments, the polymer is a methacrylated hyaluronic acid.

In some embodiments, the polymer and the insulin or bioactive derivative thereof are covalently conjugated via an amide linkage (e.g., between an amino group on the insulin or bioactive derivative thereof and a carboxylic acid group on the polymer). However, any suitable linkage (e.g., based on the available reactive groups on the polymer and the insulin) can be used to form a covalent linkage. Thus, any suitable conjugation chemistry known in the art can be used. In some embodiments, a chemical linker (e.g., such as a bifunctional linker known in the art for protein conjugation) can be used to provide a linkage between the polymer and the insulin or bioactive derivative thereof. For instance, the linker can comprise two functional groups (e.g., two different functional groups) separated by an alkylene, aralkylene, or arylene group. In some embodiments, the two functional groups are separated by a cycloalkylene or polymeric (e.g., a poly(ethylene glycol)) group. The two functional groups can be selected from the group including, but not limited to, esters, such as n-hydroxysuccinimide (NHS) esters, sulfo-NHS esters, and imidoesters, photo-reactive groups, such as aryl azides or diazerines, maleimides, and amines. In some embodiments, the polymer and the insulin can be directly conjugated to one another, e.g., via reaction with a carbodiimide coupling reagent (e.g., 1-ethyl-3-(3-dimethylaminopropyl)carbodiimide (EDC)) to form amide bonds between amino groups on the insulin and the carboxylic acid groups on the polymer. In some embodiments, a primary amine of the insulin or bioactive derivative thereof can be contacted with a thiolating agent, such as, 2-iminothiolane or another thiolating agent known in the art, to provide a thiol group that can be reacted with a suitable bifunctional linker during conjugation to the polymer.

In some embodiments, the insulin or bioactive derivative thereof can be human insulin, recombinant human insulin, insulin from a non-human animal source (e.g. bovine, porcine) or any other insulin, including insulin derivatives. In some embodiments, the insulin is of the same species as the intended recipient, i.e., human insulin for treatment of humans. The insulin or bioactive derivative thereof can include mixtures of different insulins and/or derivatives. The insulin or bioactive derivative thereof can include fast-acting insulins, rapid-acting insulin analogs, intermediate-acting insulins, and/or long-acting insulins. In some embodiments, the insulin or bioactive derivative thereof is a fast-acting or rapid-acting insulin.

Fast-acting insulins start to work within one to 20 minutes, peaking about one hour later and lasting from three to five hours. Fast-acting insulin takes about two hours to fully absorb into the systemic circulation. Fast-acting insulins include regular recombinant human insulin (such as HUMULIN™ marketed by Lilly, and NOVOLIN™, marketed by NovoNordisk). Bovine and porcine insulins, which differ in several amino acids to human insulin, but are bioactive in humans, are also fast acting insulins.

Rapid-acting insulins include insulins that have been modified or have altered locations of amino acids in order to enhance their rate of absorption. There are three types of rapid-acting commercial insulin analogs available: lispro insulin (Lysine-Proline insulin, sold by Eli Lilly as HUMALOG™), glulisine insulin (sold by Sanofi-Aventis as APIDRA™) and aspart insulin (sold by Novo Nordisk as NOVOLOG™).

Intermediate-acting insulin has a longer lifespan than short-acting insulin, but it is slower to start working and takes longer to reach its maximum strength. Intermediate-acting insulin usually starts working within 2-4 hours after injection, peaks somewhere between 4-14 hours and remains effective up to 24 hours. Types of intermediate-acting insulin include NPH (Neutral Protamine Hagedom) and LENTE™ insulin. NPH insulin contains protamine which slows down the speed of absorption so that the insulin takes longer to reach the bloodstream but has a longer peak and lifespan.

Long-acting insulins include Eli Lilly's Humulin™ U (Ultralente™ human insulin (recombinant DNA origin) extended zinc suspension); and insulin glargine (LANTUS™ Aventis). Insulin glargine is a recombinant human insulin analog that can have up to 24 hour duration. It differs from human insulin by having a glycine instead of asparagine at position 21 and two arginines added to the carboxy-terminus of the beta-chain. LANTUS™ consists of insulin glargine dissolved in a clear aqueous fluid (100 IU, 3.6378 mg insulin glargine, 30 micrograms zinc, 2.7 mg m-cresol, 20 mg glycerol 85%, and water to 1 ml).

Any suitable insulin aptamer can be used. In some embodiments, the insulin aptamer is an oligonucleotide (i.e., a single-stranded oligonucleotide). In some embodiments, the oligonucleotide comprises the sequence 5'-GGT GGT GGG GGG GGT TGG TAG GGT GTC TTC-3' (i.e., SEQ ID NO: 1) or 5'-ACA GGG GTG TGG GGA CAG GGG TGT GGGG-3' (i.e., SEQ ID NO: 2). In some embodiments, the insulin aptamer is a 5'-amino modified oligonucleotide. In some embodiments, the insulin aptamer is 5'-amino modified SEQ ID NO: 1.

Any suitable glucagon or bioactive derivative thereof can be used. In some embodiments, the glucagon has the sequence: $NH_2$—His-Ser-Gly-Gly-Thr-Phe-THr-Ser-Asp-Tyr-Ser-Lys-Tyr-Leu-Asp-Ser-Arg-Arg-Ala-Gln-Asp-Phe-Val-Gln-Trp-Leu-Met-Asm-Thr-COOH (i.e. SEQ ID NO: 3). In some embodiments, the glucagon is thiolated, e.g., via reaction with 2-iminothiolane or another suitable thiolating agent known in the art.

The glucagon and the insulin aptamer can be covalently conjugated using any suitable conjugation chemistry. In some embodiments, the glucagon is thiolated and the glucagon and the insulin aptamer are conjugated via a chemical linker that comprises two different reactive functional groups e.g., a succinimidyl ester (e.g., that can react with a primary amine to form an amide) and a maleimidyl group (e.g., that can react with a thiol group to form a C—S bond. The chemical inker can include an alkylene, arylene or aralkylene group between the two reactive functional groups. In some embodiments, the alkylene group can be polymeric or oligomeric (e.g., can comprise a divalent poly(ethylene glycol) moiety). In some embodiments, the alkylene group comprises a divalent cyclohexane moiety and the chemical linker is sulfosuccinimidyl-4-(N-maleimidomethyl)-cyclohexane-1-carboxylate (Sulfo-SMCC).

The polymer-insulin conjugate and the insulin aptamer-glucagon conjugate can associate non-covalently (e.g., when the insulin aptamer binds to the insulin) to form a glucagon-polymer conjugate. When the polymer is methacrylated hyaluronic acid, the glucagon-polymer conjugate is a glucagon-hyaluronic acid (Glu-HA) conjugate.

In some embodiments, the composition can be cross-linked. For example, in some embodiments, a suitable crosslinker can be added to the composition and a cross-linking reaction initiated via a suitable approach, such as via UV radiation, addition of a chemical catalyst/initiator and/or via heat, in order to form a cross-linked matrix. In some embodiments, the cross-linked matrix is a hydrogel. In some embodiments, the crosslinker is N,N'-methylenebisacrylamide. Suitable photoinitiators include, but are not limited to, alpha hydroxyketones and bis acyl phosphine oxides (BAPOs). In some embodiments, a further therapeutic agent can be incorporated in the hydrogel (e.g., covalently or non-covalently).

In some embodiments, the presently disclosed composition is provided in the form of a pharmaceutical composition where the Glu-polymer conjugate is provided with a pharmaceutically acceptable carrier, e.g., a carrier suitable for intravenous or sub-cutaneous injection. In some embodiments, the carrier or excipient is pharmaceutically acceptable for use in humans. In some embodiments, the carrier or excipient is acceptable for use in animals (e.g., in veterinary settings). In some embodiments, the pharmaceutically acceptable carrier can be a liquid, such as water, saline, glycerol and/or ethanol. Additionally, auxiliary substances, such as wetting or emulsifying agents or pH buffering substances, can be present in such compositions.

In some embodiments, the Glu-polymer conjugate is provided in a form suitable for transdermal delivery. For instance, in some embodiments, the presently disclosed subject matter provides a microneedle (MN) array comprising a Glu-polymer conjugate as described herein. In some embodiments, the microneedle array can comprise a plurality of microneedles wherein each of said plurality of microneedles has a length of between about 20 and about 1000 microns (e.g., about 20, 50, 100, 150, 200, 250, 300, 350, 400, 450, 500, 550, 600, 650, 700, 750, 800, 850, 900, 950, or about 1000 microns). In some embodiments, each of the plurality of microneedles has a length of between about 500 microns and about 700 microns. In some embodiments, each microneedle can have an approximately conical or pyramidal shape. In some embodiments, the tip of the microneedles can be less than about 100 microns, less than about 75 microns, less than about 50 microns, less than about 40 microns, less than about 30 microns, or less than about 20 microns. In some embodiments, the tip of each of the microneedles can be about 10 microns.

The microneedle array can comprise a plurality of microneedles, wherein the bases of microneedles are arranged in any suitable two-dimensional pattern. The microneedles can be arranged in a regular array (e.g., a square, rectangular, circular, oval or other shaped pattern) wherein the distance between individual microneedles remains the same or varies in a repeating fashion, or in an irregular array (e.g., wherein the distance between individual microneedles varies in no recognizable repeating fashion).

In some embodiments, the microneedle array can be provided as part of a skin patch. In some embodiments, the microneedle array can comprise one or more backing layers (e.g., to protect the microneedle array from moisture or physical insult (e.g., scratches). In some embodiments, the microneedle array can comprise a layer that extends outward from the array (e.g., coplanar to the base of the array) that comprises a skin-compatible adhesive for aiding in the attachment of the array to the skin.

The presently disclosed compositions and/or microneedle arrays can release glucagon or a bioactive derivative thereof in an insulin-responsive or dependent manner. In some embodiments, the release rate of the glucagon or bioactive derivative is dependent upon the concentration of insulin coming into contact with the array (e.g., the release rate is faster when the array is in contact with higher concentrations of insulin). Thus, in some embodiments, the composition and/or microneedle array is a closed-loop glucagon delivery system.

In some embodiments, one or more additional therapeutic agent is contained within the MNs and can be released along with the glucagon or bioactive derivative thereof. In some embodiments, the additional therapeutic agent is water-soluble. In some embodiments, the additional therapeutic agent is a protein or protein derivative. In some embodiments, the additional therapeutic agent is an agent for treating diabetes or a complication thereof.

In some embodiments, the subject treated according to the presently disclosed subject matter is a human subject, although it is to be understood that the methods described herein are effective with respect to all vertebrate species, which are intended to be included in the term "subject."

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Thus, embodiments of the methods described herein include the treatment of livestock, including, but not limited to, domesticated swine (pigs and hogs), ruminants, horses, poultry, and the like.

In some embodiments, the subject is diabetic. The subject can have type 1 or type 2 diabetes. In some embodiments, the subject is being treated with insulin replacement therapy (e.g., injected insulin), a sulfonylurea, and/or a meglitinide. In some embodiments, the insulin replacement therapy is performed simultaneously to application of the presently disclosed patch.

In some embodiments, the subject is non-diabetic and suffers from hyperinsulinemic hypoglycemia. In some embodiments, the subject has a disease or disorder resulting in increased circulating insulin selected from the group including, but not limited to, congenital hyperinsulinism, an insulinoma, gastric dumping syndrome, autoimmune insulin syndrome, or reactive hypoglycemia.

In some embodiments, the presently disclosed subject matter provides a polymer-insulin conjugate and an insulin aptamer-glucagon conjugate for use in treating and/or preventing hypoglycemia, e.g., hyperinsulinemic hypoglycemia or a disease or disorder resulting in increased circulating insulin selected from the group including, but not limited to, congenital hyperinsulinism, an insulinoma, gastric dumping syndrome, autoimmune insulin syndrome, or reactive hypoglycemia.

In some embodiments, the presently disclosed subject matter provides the use of a polymer-insulin conjugate and an insulin aptamer-glucagon conjugate for the preparation of a pharmaceutical composition for treating and/or preventing hypoglycemia, e.g., hyperinsulinemic hypoglycemia or a disease or disorder resulting in increased circulating insulin selected from the group including, but not limited to, congenital hyperinsulinism, an insulinoma, gastric dumping syndrome, autoimmune insulin syndrome, or reactive hypoglycemia.

In some embodiments, the presently disclosed subject matter provides a method of preparing a microneedle array for the insulin-responsive delivery of glucagon or a bioactive derivative thereof. In some embodiments, the method comprises:

(a) providing a mold comprising one or more microcavities;
(b) filling at least a portion of the one or more microcavities with a first solution comprising: (i) a composition of a polymer-insulin conjugate and a insulin aptamer-glucagon conjugate, (ii) a crosslinking agent; and, optionally, (iii) a photoinitiator;
(c) drying the filled mold to remove water;
(d) removing the mold to provide a microneedle array; and
(e) crosslinking the microneedle array to provide a crosslinked microneedle array.

The crosslinking can be performed via any suitable method, e.g., using heat, UV radiation and/or a chemical catalyst/initiator. In some embodiments, the first solution comprises a photoinitiator and the crosslinking is performed via UV radiation. In some embodiments, a portion of the mold (e.g., a portion of the microcavities closer to the base of the microcavities) is filled with a second solution that does not contain the polymer-insulin conjugate and the insulin aptamer-glucagon conjugate. In some embodiments, the second solution comprises a crosslinkable polymer and optionally a crosslinker and/or a photoinitiator. In some embodiments, the second solution can contain the same polymer used to prepare the polymer-insulin conjugate. In some embodiments, the second solution comprises methacrylated hyaluronic acid, a crosslinking agent, and a photoinitiator.

In some embodiments, the filling of the mold in step (b) can be performed under vacuum and/or can involve centrifuging the mold (e.g., to aid in efficient and/or increased packing of the conjugate solution in the microneedle cavities). In some embodiments, the mold can be dried in a vacuum desiccator.

In some embodiments, the mold can comprise a polymer, such as silicone (e.g., polydimethylsiloxane (PDMS)). The mold can comprise about 10, 50, 100, 250, 500, 1000 or more microcavities. The tip-to-tip spacing between tips of the microcavities can be between about 100 microns and about 1000 microns (e.g., about 100, 150, 200, 250, 300, 350, 400, 450, 500, 550, 600, 650, 700, 750, 800, 850, 900, 950, or about 1000 microns).

Figure 6:
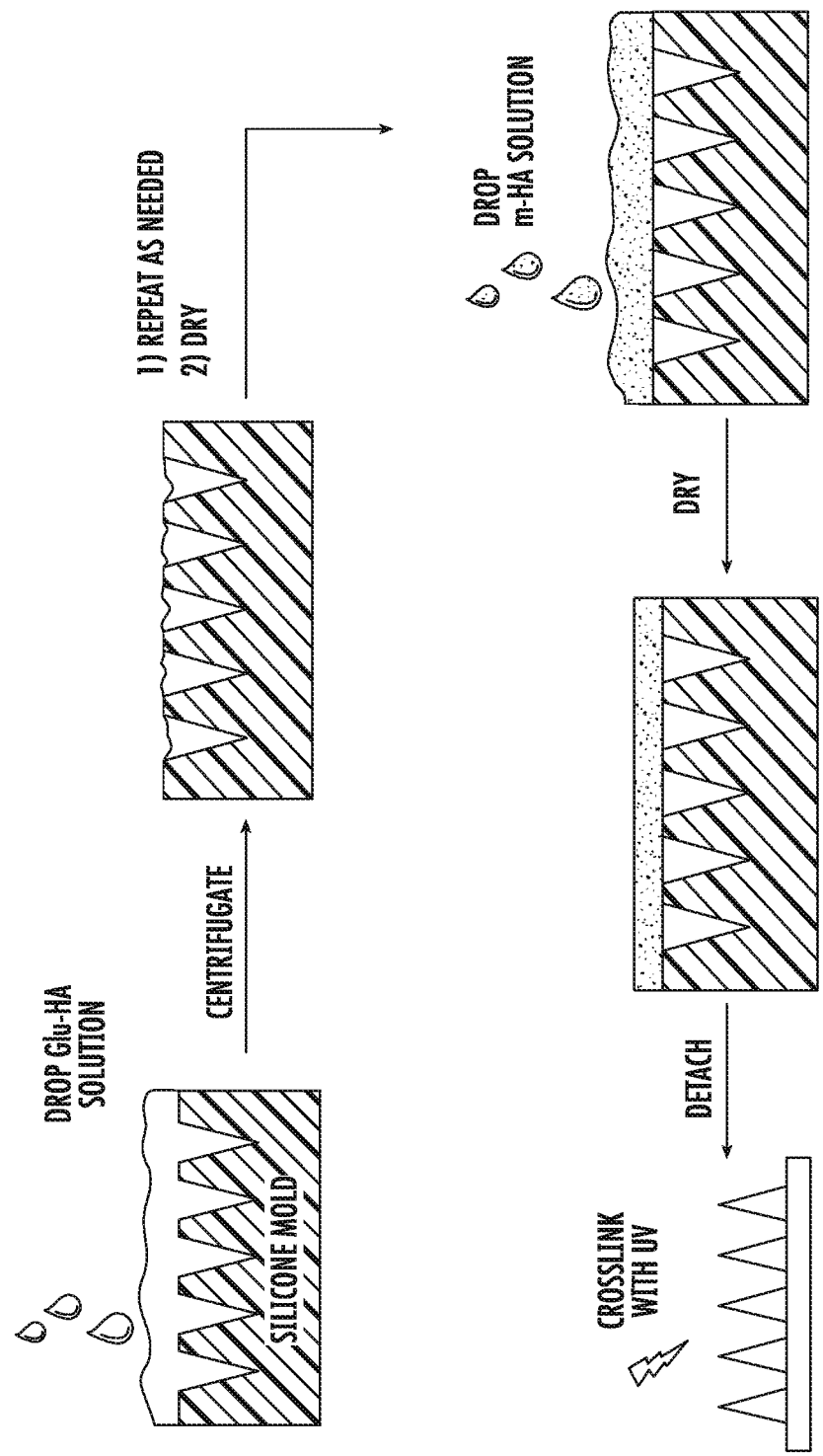
FIG. 6 is a schematic drawing of an exemplary process for preparing an insulin-responsive glucagon delivery microneedle (MN) array patch of the presently disclosed subject matter using a silicone mold.

FIG. 6 shows a schematic diagram of an exemplary method for preparing a microneedle array of the presently disclosed subject matter. A solution comprising a composition comprising a polymer-insulin conjugate and an insulin aptamer-glucagon conjugate (e.g., a composition comprising an insulin-responsive glucagon-polymer conjugate, such as Glu-HA) is dropped into a silicone mold comprising a plurality of microcavities (e.g., using a micropipette). The solution can also comprise a crosslinking agent and a photoinitiator. The filled mold is centrifuged to eliminate any remaining air from the microcavities. The dropping and centrifuging steps can be repeated one or more times (e.g., one, two, three or more times), as needed, to fill the microcavities. Then, the filled mold is dried, e.g., under vacuum conditions. After drying, a polymer solution (e.g., a m-HA solution), optionally comprising a crosslinking agent or a crosslinking agent and a photoinitiator, is dropped onto the mold and dried, forming a polymer layer over the top of the filled microcavities. Then the resulting dried MN patch is detached from the mold and exposed to UV radiation of a period of time to initiate crosslinking of the polymer(s).

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Synthesis of Apt-Glu, Ins-HA, and Glu-HA Hydrogel

Materials:
All chemicals were purchased from Sigma-Aldrich (St. Louis, Missouri, United States of America) unless otherwise specified and were used as received. Human recombinant insulin (Zn salt, 27.5 IU/mg) was purchased from Life Technology (Thermo Fisher Scientific, Waltham, Massachusetts, United States of America). Amino modified insulin binding aptamer was purchased from Integrated DNA Technologies Inc. (Coralville, Iowa, United States of America): 5'-$H_2N$-GGT GGT GGG GGG GGT TGG TAG GGT GTC TTC-3' (SEQ ID NO: 4).

Synthesis of Apt-Glucagon: Glucagon or FITC-labelled glucagon was thiolated by reacting with the glucogon or FITC-labelled glucagon with Traut's Reagent (2-iminothiolane, Thermo Fisher Scientific, Waltham, Massachusetts, United States of America) in PBS (pH 8.0) at a molar ratio of 1:10 for 1 h at room temperature (RT). Excess Traut's Reagent was removed using a centrifugal filter device (molecular weight cut-off (MWCO)=3 kiloDalton (kDa)). In the meantime, amino modified insulin aptamer was mixed with sulfosuccinimidyl-4-(N-maleimidomethyl)-cyclohexane-1-carboxylate (Sulfo-SMCC, Thermo Fisher Scientific, Waltham, Massachusetts, United States of America) in PBS (pH=7.4) at a molar ratio of 1:5 for 0.5 h at RT. The activated aptamer was purified using a Nap-5 column. Finally, the purified aptamer and glucagon-SH was mixed in PBS (pH 8.0) at a molar ratio of glucagon:aptamer=1:2. After 24-h reaction at 4° C., the obtained Apt-Glu was purified using a Nap-5 column, and stored at 4° C. until use. MALDI MS confirmed the formation of the Apt-Glu conjugate, indicating a molecular weight for the conjugate of about 13,528.

Synthesis of m-HA:
m-HA was synthesized follow a previously published procedure. See Jiang et al., Adv. Funct. Mater., 24, 2295 (2014). Briefly, 1.0 g of HA was dissolved in 50 mL of DI water at 4° C., to which 0.8 mL of methacrylic anhydride (MA) was dropwise added. The reaction solution was adjusted to pH 8-9 by the addition of 5 N NaOH and stir at 4° C. for 24 h. The resulting polymer was obtained by precipitation in acetone, followed by washing with ethanol for 3 times. The product re-dissolved in DI water and the solution dialyzed against DI water for 2 days. m-HA was achieved by lyophilization with a yield of 87.5%. The degree of modification was calculated to be 15% by comparing the ratio of the areas under the proton peaks at 5.74 and 6.17 ppm (methacrylate protons) to the peak at 1.99 ppm (N-acetyl glucosamine of HA) after performing a standard deconvolution algorithm to separate closely spaced peaks. Number average molecular weight ($M_n$)=341,149 g/mol. $^1$H NMR (300 MHz, $D_2O$, δ): 1.85-1.96 (m, 3H, $CH_2$=C($CH_3$)CO), 1.99 (s, 3H, $NHCOCH_3$), 5.74 (s, 1H, $CH^1H^2$=C($CH_3$)CO), 6.17 (s, 1H, $CH^1H^2$=C($CH_3$)CO).

Synthesis of Ins-HA:
60 mg of m-HA was dissolved in water, to which 1-ethyl-3-(3-dimethylaminopropyl)carbodiimide (EDC) (0.19 g)

and N-hydroxysuccinimide (NHS) (0.13 g) were added and stirred for 15 min at RT. Then insulin (30 mg) was added to the mixture and reacted at 4° C. for 24 h. The reaction solution was thoroughly dialyzed against DI water for 1 day. Finally, Ins-HA was obtained by lyophilization. M=431,475 g/mol.

Preparation of Glu-HA Hydrogel:

Crosslinker N,N-methylenebisacrylamide (MBA, w/v=2%) and photoinitiator (Irgacure 2959, w/v=0.5%) were mixed in Glu-HA solution. After UV irradiation (wavelength: 365 nm) for 60 s, the mixture underwent the cross-linking polymerization to form the hydrogel.

Fabrication of Glu-HA Loaded MN:

MNs were fabricated using uniform silicone molds from Blueacre Technology Ltd. (Dundalk, Ireland). Each needle had a 300 µm by 300 µm round base tapering to a height of 600 µm with a tip radius of around 10 µm. The needles were arranged in a 15×15 array with 600 µm tip-to-tip spacing. Before the fabrication of the Glu-HA loaded MN, the solution for the preparation of both the tips and base of MN were sterilized using 0.22 µm syringe filters, and the MN molds were sterilized by ultraviolet light. The whole preparation was performed in a sterile manner. Glu-HA solution with N,N-Methylenebisacrylamide (MBA, w/v=2%), photoinitiator (Irgacure 2959, w/v=0.5%) was first deposited by pipet onto the MN mold surface (50 µL/array). See FIG. 6. Afterwards, molds were placed under vacuum (600 mmHg) for 5 min to allow the solution filled the MN cavities and became more viscose. Then, the covered molds were centrifuged using a Hettich Universal 32R centrifuge (Hettich GmbH & Co. KG, Tuttlingen, Germany) for 20 min at 2000 rpm to make sure there was no air retained in the cavities of MN. The process was repeated for three times until the solution layer was dried in the vacuum condition. For better MNs morphology, a piece of 4 cm×9 cm silver adhesive tape was applied around the 2 cm×2 cm micromold baseplate. Finally, 3 mL premixed MBA (w/v=2%), photoinitiator (Irgacure 2959, w/v=0.5%) and m-HA solution was added into the prepared micromold reservoir and allowed to dry at 25° C. under vacuum dessicator overnight. After completely desiccation, the MN-arrays patch was carefully separated from the silicone mold and underwent the crosslinking polymerization via UV irradiation (wavelength: 365 nm) for a short period of time. The resulting MN-array patches were stored in a sealed six well container at 4° C. for later study. The loading capability of glucagon in the MN-array patch is 0.63%. The morphology of the MNs was characterized on a FEI Verios 460L field-emission scanning electron microscope (FESEM) (FEI, Hillsboro, Oregon, United States of America).

Mechanical Strength Test:

The mechanical strength of MNs with a stress-strain gauge was measured by pressing MNs against a stainless steel plate. The initial gauge was set as 2.00 mm between the MNs tips and the stainless steel plate, 10.00 N as load cell capacity. The speed of the top stainless steel plate movement towards the MN-array patch was 0.1 mm/s. The failure force of MNs was recorded as the needle began to buckle.

Example 2

In Vitro and In Vivo Studies:

In Vitro Release Studies: After preparation of the FITC-Glu-HA hydrogel, various PBS solutions with 0, 0.1, 0.5, and 1 mg/mL insulin were added to each tube and incubated at 37° C. on an orbital shaker. At predetermined time points, the sample was centrifuged (8000 rpm, 30 s) and 100 µL of the supernatant was removed for analysis by measuring the emission intensity of FITC at 519 nm with the excitation wavelength at 495 nm.

Biocompatibility Analysis:

To evaluate the biocompatibility of the MN-array patches, mice were euthanized by $CO_2$ asphyxiation and the surrounding tissues were excised after 24-hour administration. The tissues were fixed in 10% formalin and then embedded in paraffin, cut into 50-µm sections, and stained using hematoxylin and eosin (H&E) for histological analysis.

In Vivo Studies Using STZ-Induced Diabetic Mice: The in vivo performance of MN-array patches was evaluated on STZ-induced adult diabetic mice (male C57B6, Jackson Lab, Bar Harbour, Maine, United States of America). The plasma-equivalent glucose was measured from tail vein blood samples (~3 µL) of mice using the Clarity GL2Plus glucose meter (Clarity Diagnostics, Boca Raton, Florida, United States of America). Mouse glucose levels were monitored for two days before administration, and all mice were fasted overnight before administration. Five mice for each group were selected to be transcutaneously treated with blank MNs containing only m-HA or Glu-HA loaded MNs. Afterwards, a high-dose insulin (100 µg) or a low-dose insulin (20 µg) was subcutaneously injected into each mouse. The glucose levels of each mouse were monitored over time. In order to measure the plasma glucagon concentration in vivo, 25 µL of blood sample was drawn from the tail vein of mice at indicated time points. The serum was isolated and stored at −20° C. until assay. The plasma glucagon concentration was measured using Human Glucagon ELISA Kit (Thermo Fisher Scientific, Waltham, Massachusetts, United States of America).

Statistical Analysis:

All results presented are Mean±s.d. Statistical analysis was performed using Student's t-test or ANOVA test. With a P value <0.05, the differences between experimental groups and control groups were considered statistic.

Example 3

Discussion of Examples 1 and 2

Figure 2:
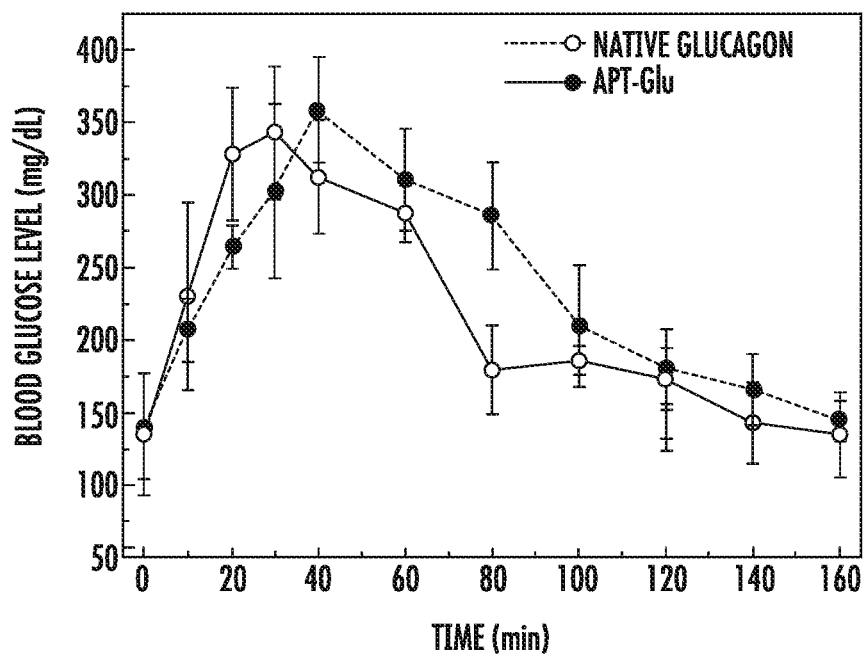
FIG. 2 is a graph showing time dependent blood glucose changes (measured in milligrams per deciliter (mg/dL)) of healthy mice after injection of native glucagon (open circles with dotted line) or an aptamer-glucagon conjugate (Apt- Glu; filled circles with solid line). Blood glucose was measured for up to 160 minutes (min) after injection.

As described in Example 1, in order to prepare insulin-responsive Glu-HA, insulin conjugated m-HA (Ins-HA) and insulin aptamer modified glucagon (Apt-Glu) were first prepared. The covalent coupling of insulin onto m-HA was achieved by formation of an amide bond between the primary amino groups of insulin and the carboxylic acid groups of the m-HA. The Apt-Glu conjugate was obtained from the amino-modified aptamer and thiolated glucagon via a heterobifunctional linker. The successful modification of glucagon was clearly identified by matrix-assisted laser desorption/ionization mass spectrometry (MALDI MS). The bioactivity of the resulting Apt-Glu conjugates was confirmed upon administration to the healthy mice when compared to the native glucagon. See FIG. 2. After co-incubating Apt-Glu and Ins-HA in TKN buffer (50 mM Tris-HCl, 10 mM KCl, 100 mM NaCl, pH 8.0), Apt-Glu bound to Ins-HA to form insulin-responsive Glu-HA through specific interaction between the binding aptamer and target insulin.

Upon the addition of a crosslinker, e.g., N,N'-methylenebisacrylamide, and a photoinitiator, Glu-HA forms a hydrogel by photo-polymerization after UV irradiation for a short period of time. To assess the ability of Glu-HA to respond to insulin, the prepared hydrogels were incubated with 1×PBS buffer [137 mM NaCl, 2.7 mM KCl, 10 mM $Na_2HPO_4$, 2 mM $KH_2PO_4$ (pH 7.4)] at increasing insulin concentrations.

Figure 3B:
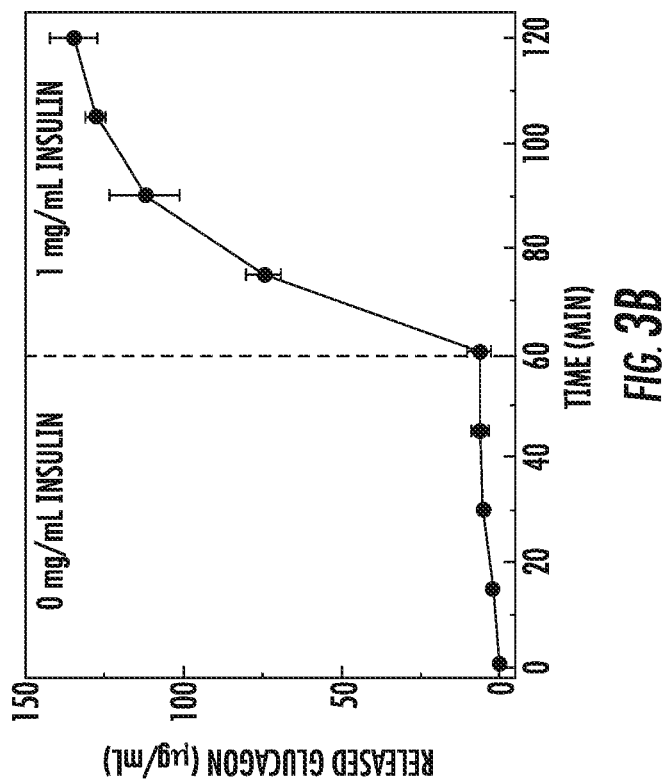
FIG. 3B is a graph showing the in vitro release rate of glucagon (measured in micrograms per milliliter (μg/mL)) from a Glu-HA hydrogel as a function of insulin concentration when insulin concentration changes in a pulsatile manner. From time 0 minutes (min) to time 60 min (left half of graph), the insulin concentration is 0 milligrams per milliliter (mg/mL). After 60 minutes (right half of graph) the hydrogel is exposed to an insulin concentration of 1 mg/mL.
Figure 3A:
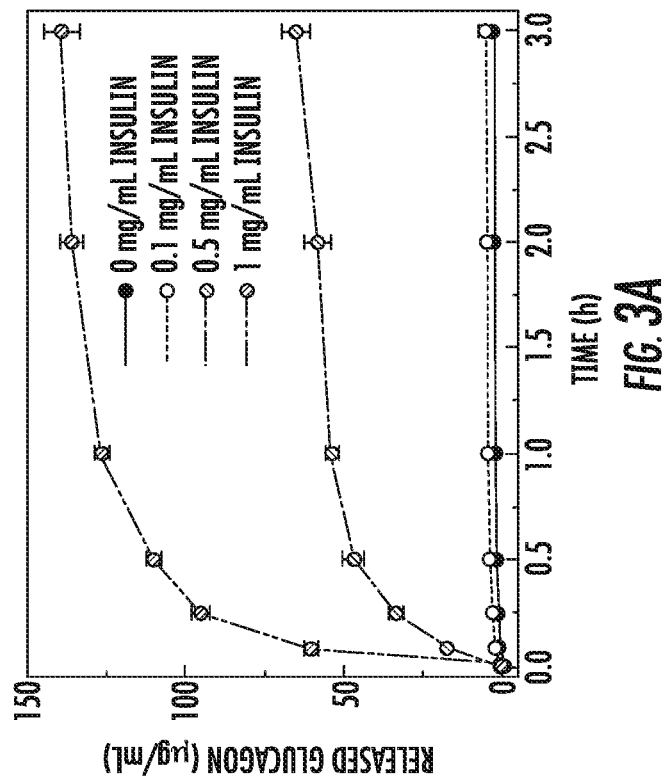
FIG. 3A is a graph showing the in vitro accumulated glucagon release (measured in micrograms per milliliter (μg/mL)) from a glucagon-hyaluronic acid (Glu-HA) hydrogel at different insulin concentrations: (0 milligrams per milliliter (mg/mL) (filled circles with solid line), 0.1 mg/mL (open circles with dotted line), 0.5 mg/mL (circles with stripes going from bottom left to top right), or 1 mg/mL (circles with stripes going from top left to bottom right) at 37° C. The glucagon release is measured from 0 to 3 hours (h).

As presented in FIG. 3A, the release rate of glucagon from the Glu-HA hydrogel was highly dependent on the concentration of insulin, such that the hydrogel incubated with 1 mg/mL insulin showed the fastest release rate compared to hydrogel incubated with 0, 0.1, and 0.5 mg/mL insulin. The insulin responsiveness of the Glu-HA hydrogel was further verified by rapidly changing the insulin concentration in the solution and measuring glucagon release rate. The Glu-HA hydrogel was stable in PBS buffer without insulin. When adding 1 mg/mL insulin to the solution, the Glu-HA hydrogel quickly released glucagon. See FIG. 3B. Without being bound to any one theory, this insulin-responsive release of glucagon is believed to be attributable to the competitive binding between free insulin and insulin conjugated on m-HA to their specific aptamer on the Apt-Glu conjugate.

Figure 4A:
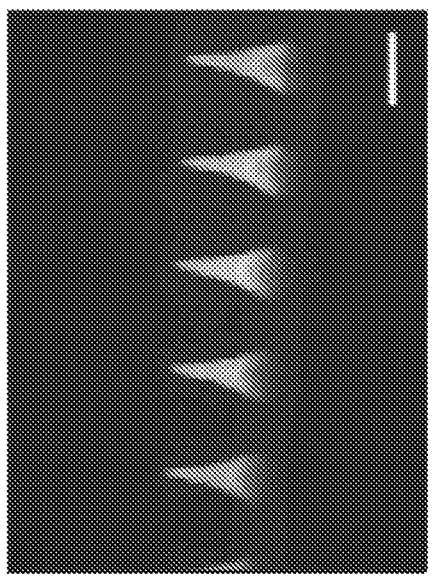
FIG. 4A is a microscopy image of a microneedle (MN)-array patch of the presently disclosed subject matter. The scale bar in the lower right represents 1 millimeter (mm).
Figure 4B:
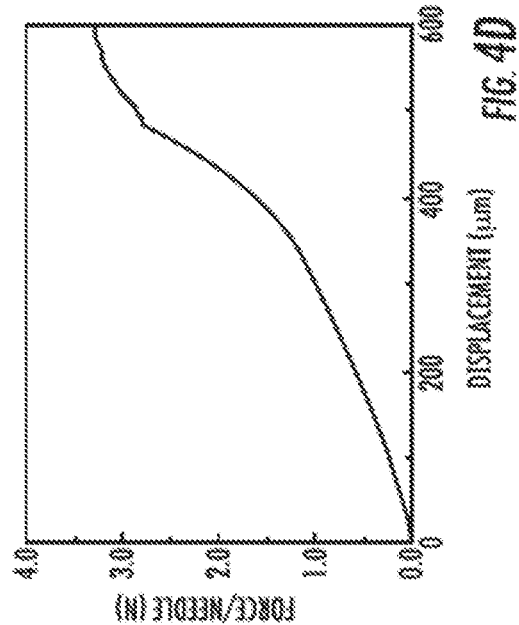
FIG. 4B is a fluorescence microscopy image of rhodamine-labelled MN loaded with fluorescein isothiocyanate (FITC)-labeled glucagon-hyaluronic acid (Glu-HA). The scale bar in the lower right represents 500 micrometers (μm).
Figure 4C:
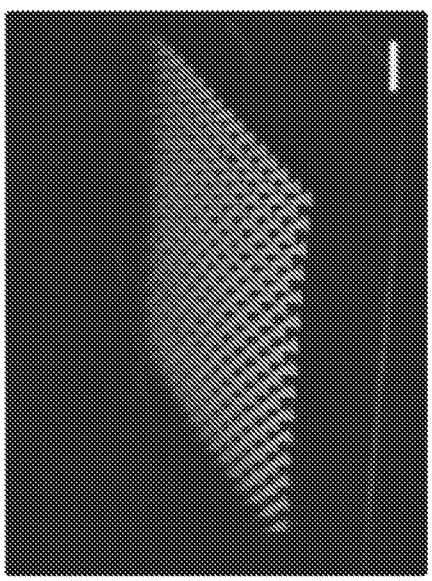
FIG. 4C is a scanning electron microscopy (SEM) image of a microneedle (MN) array of the presently disclosed subject matter. The scale bar in the lower right represents 200 μm.
Figure 4D:
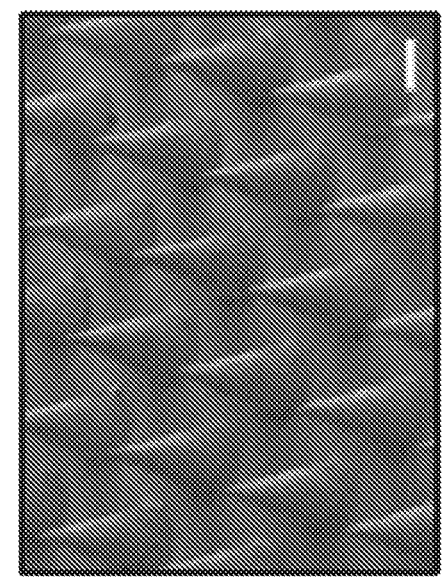
FIG. 4D is a graph of the mechanical behavior (force per needle (in Newtons (N)) versus displacement (in μm)) of a glucagon-hyaluronic acid (Glu-HA)-loaded MN.

A microneedle (MN)-based transdermal delivery system was chosen to achieve a painless, convenient, and long-term administration. In order to fabricate drug-loaded MN, Glu-HA, the crosslinker N,N-methylenebisacrylamide, and a photoinitiator were first loaded in the tip region of a silicone mold of MN-array patch through centrifugation. After exposure to UV irradiation for 60 s, the HA matrix containing glucagon was formed by photo-crosslinking, which can aid in limiting diffusion of Glu-HA in vivo, and also enhances the stiffness of MNs for penetration. The prepared MNs were arranged in a 15×15 array. See FIG. 4A. Each MN is conically shaped and about 300 μm in diameter at the base and about 600 μm in height. See FIG. 4C. To further confirm the distribution of Glu-HA in the MNs, a FITC-labelled Glu-HA loaded patch was imaged by fluorescence microscopy. See FIG. 4B. Based on the localization of fluorescence from the FITC-labelled Glu-HA in the tip portions of the array, imaging appeared to confirm that Glu-HA was mainly located in the tips of MNs. Using a tensile compression machine, the failure force for crosslinked MN was determined to be 2.8 N/needle (see FIG. 4D), which is sufficient to penetrate skin without breaking. See Prausnitz, Advanced Drug Delivery Reviews, 56, 581 (2004). The Glu-HA loaded MNs exhibited similar insulin-responsive capability compared to the hydrogel.

Figure 5A:
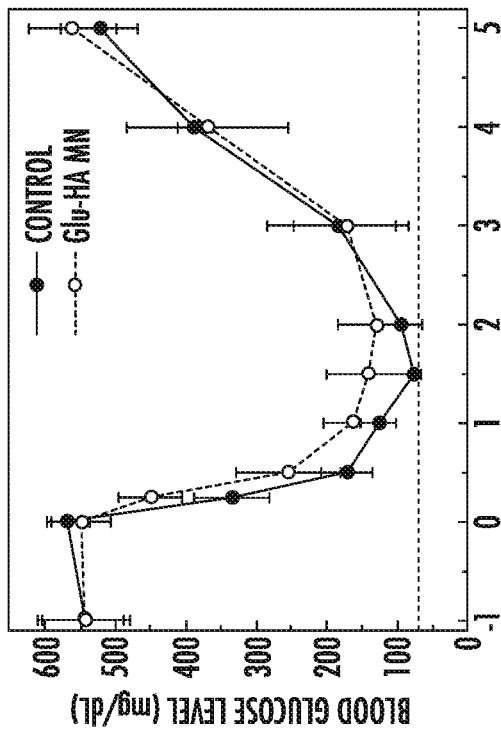
FIG. 5A is a graph showing data from an in vivo study of a glucagon-hyaluronic acid (Glu-HA) loaded microneedle (MN)-array patch in the prevention of hypoglycemia. The graph shows the blood glucose level (BGL) (measured in milligrams per deciliter (mg/dL)) in streptozotocin (STZ)-induced type 1 diabetic mice treated with glucagon-hyaluronic acid (Glu-HA) loaded microneedles (Glu-HA MN, open circles with dotted line) prior to and after injection with a high dose of insulin (100 micrograms (μg)). BGL is also provided for diabetic mice (Control, filled circles with solid line) injected with the high dose of insulin, but not treated with the Glu-HA-loaded MNs. Data is measured starting one hour prior to insulin injection (−1 hour (h)) up to 5 hours after insulin injection.
Figure 5B:
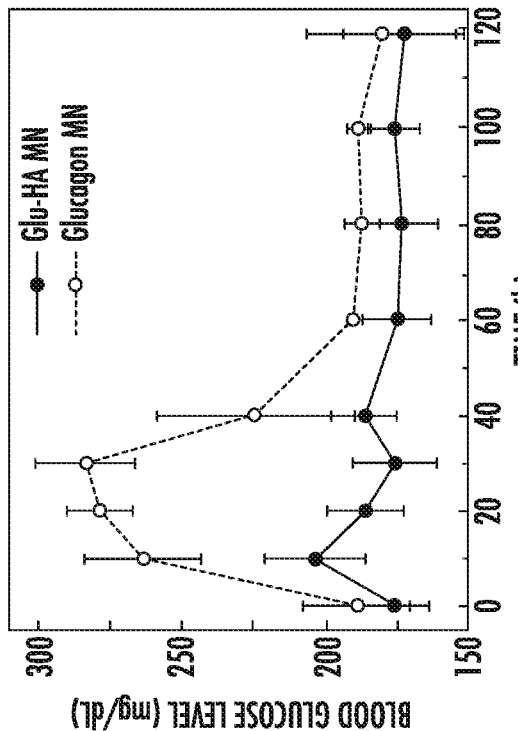
FIG. 5B is a graph of blood glucose level (BGL) (measured in milligrams per deciliter (mg/dL)) in streptozotocin (STZ)-induced type 1 diabetic mice treated with glucagon-hyaluronic acid (Glu-HA) loaded microneedles (Glu-HA MN, open circles with dotted line) prior to and after injection with a low dose of insulin (20 micrograms (μg)). BGL is also provided from mice (Control, filled circles with solid line) injected with the low dose of insulin, but not treated with the Glu-HA-loaded MNs. Data is measured starting one hour prior to insulin injection (−1 hour (h)) up to 5 hours after insulin injection.
Figure 5C:
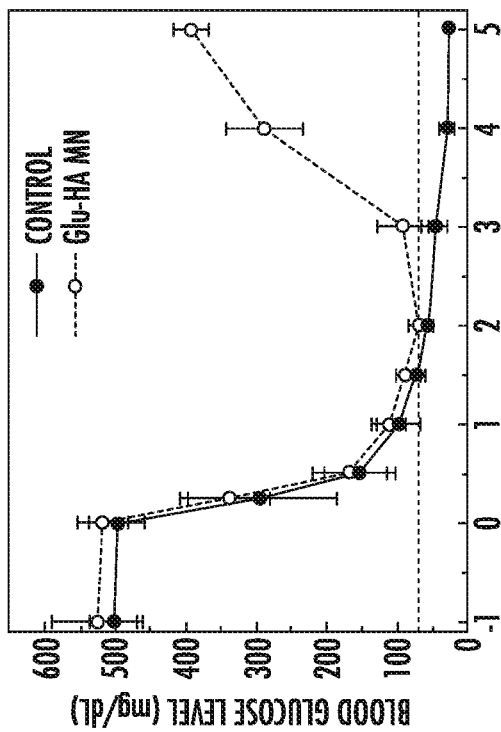
FIG. 5C is a graph showing the blood glucagon concentration (in pictograms per milliliter (pg/mL) in the mice described for FIGS. 5A and 5B. Data from control mice from FIG. 5A (high-dose insulin (Ins) Control) is shown in open circles with a dotted line; data from microneedle treated mice from FIG. 5A (High-dose Ins Glu-HA MN) is shown in filled circles with a solid line; data from control mice from FIG. 5B (low-dose Ins Control) is shown in striped circles with a broken line; and data from microneedle treated mice from FIG. 5B (low-dose Ins Glu-HA MN) is shown in striped circles with a heavy solid line.
Figure 5D:
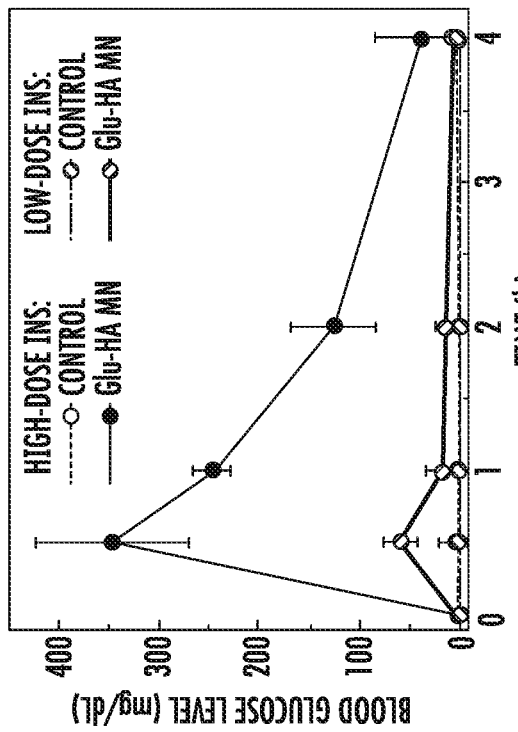
FIG. 5D is a graph showing the blood glucose changes of healthy mice administered with glucagon-hyaluronic acid (Glu-HA) loaded microneedles (Glu-HA MN, filled circles with solid line) or free glucagon-loaded microneedles (Glucagon MN, open circles with dotted line). Blood glucose levels are measured in milligrams per deciliter (mg/dL).
Figure 5E:
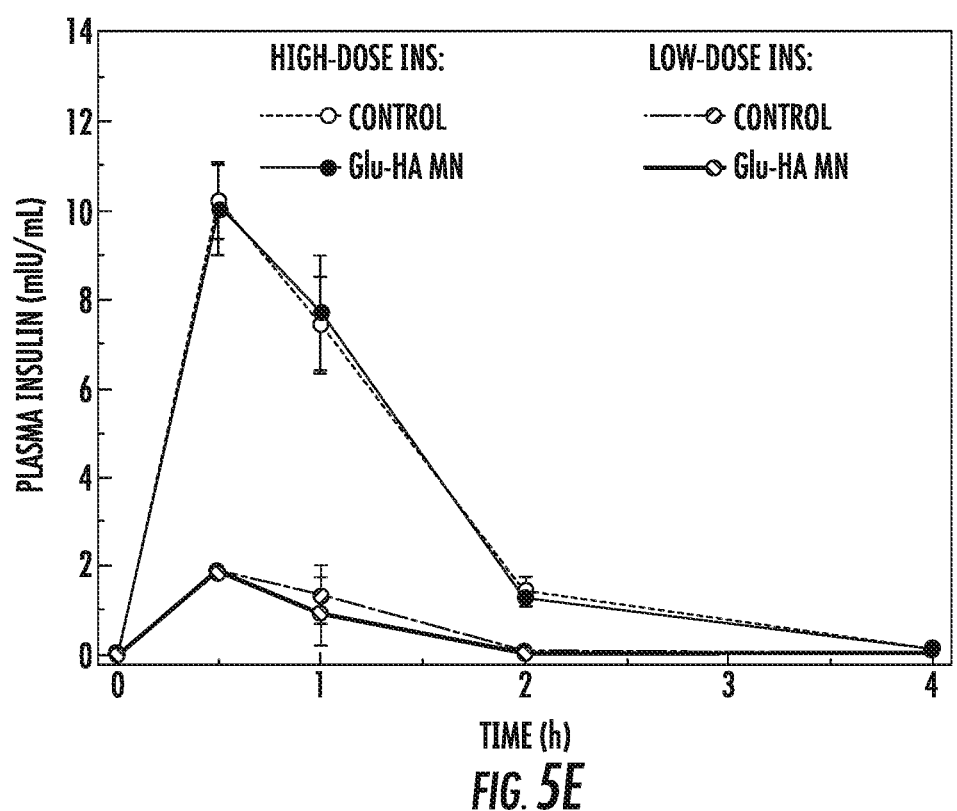
FIG. 5E is a graph showing the blood insulin concentration (in milli-international units per milliliter (mIU/mL)) in the mice described for FIGS. 5A and 5B. Data from control mice from FIG. 5A (high-dose insulin (Ins) Control) is shown in open circles with a dotted line; data from microneedle treated mice from FIG. 5A (High-dose Ins Glu-HA MN) is shown in filled circles with a solid line; data from control mice from FIG. 5B (low-dose Ins Control) is shown in striped circles with a broken line; and data from microneedle treated mice from FIG. 5B (low-dose Ins Glu-HA MN) is shown in striped circles with a heavy solid line.

Next, the in vivo insulin-responsive performance of Glu-HA loaded MNs were tested in an STZ-induced type 1 diabetic mouse model. Prior to a subcutaneous injection of insulin, the drug loaded MN-array patch was administered on the dorsum of mice. The successful penetration of MNs was affirmed by the trypan blue staining of dorsum skin. In addition, the hematoxylin and eosin (H&E) staining result showed the MN could be removed intact from skin, indicating its minimal side effect. Mice were injected with a high dose of insulin sufficient to cause profound hypoglycemia and the BGLs of the treated mice were monitored over time. As shown in FIG. 5A, the BGLs of the mice in the control group rapidly decreased to normal range (<200 mg/dL) within 0.5 h, and continued to decline to a hypoglycemic state (<70 mg/dL). The long-term hypoglycemia caused the death of the mice. In contrast, the BGLs of the mice with Glu-HA loaded MNs was maintained at 80 mg/dL for 2 h, and then slowly returned to hyperglycemia, which indicated the Glu-HA loaded MNs were able to respond to high insulin level and release glucagon into the regional lymph and capillary vessels to avoid the risk of hypoglycemia. As expected, the serum glucagon levels in mice administered with Glu-HA loaded MNs significantly increased following the increase of insulin concentration. See FIGS. 5C and 5E.

To further assess the responsiveness and the potential for inappropriate release of glucagon by Glu-HA loaded MNs, mice with and without patches were subcutaneously injected with a low dose of insulin. The BGLs of mice in both groups declined to normal state and began to increase 2 h post-injection. See FIG. 5B. Finally, the BGLs returned to hyperglycemia within the similar time period. The mice with MNs also presented reduced serum glucagon levels compared to those injected with the high dose of insulin, suggesting that glucagon release was directly responsive to serum insulin levels. See FIG. 5C. Finally, Glu-HA loaded MNs were tested on healthy mice. Unlike the free glucagon-loaded MN, which led to rapid increase in BGL due to the burst release of glucagon, the mice treated Glu-HA loaded MNs did not show significant changes in BGLs (see FIG. 5D), indicating there was little leak in Glu-HA MNs in healthy mice. Since HA is highly biocompatible and biodegradable, no significant inflammation was observed around the region 24 h post-administration of Glu-HA MN. Collectively, the Glu-HA-loaded MNs have capability to release glucagon in a serum insulin level dependent manner to prevent hypoglycemia in insulin replacement therapy.

In summary, an MN-array patch-based approach for insulin-triggered delivery of glucagon has been provided. Through competitive binding between free insulin and immobilized insulin on HA to insulin aptamer-modified glucagon, the drug-loaded HA matrix can effectively release glucagon under high insulin concentrations, but does not release glucagon without insulin. In vivo studies in a type 1 diabetic mouse model demonstrated that the insulin-responsive MN-array patch was able to prevent hypoglycemia after injection of a high dose of insulin sufficient to cause hypoglycemia, while showing insignificant action in mice treated with a low dose of insulin. Thus, it is believed that this glucagon patch can be useful, for instance, in improving the health, as well as the quality of life, of type 1 and advanced type 2 diabetic patients by both facilitating insulin intensification with reduced risk of hypoglycemia and preventing morbidity and mortality from severe episodes of hypoglycemia. This aptamer-incorporated controlled release method can also be extended to engineer other closed-loop therapeutic delivery systems to treat a variety of other diseases.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A composition comprising:
   (a) a polymer-insulin conjugate comprising a polymer covalently conjugated to insulin or to a bioactive derivative thereof, wherein said polymer is a hydrophilic polymer selected from the group consisting of a polysaccharide, polyglutamic acid, and a hydrophilic synthetic block copolymer, and wherein the insulin or bioactive derivative thereof is selected from the group consisting of a human insulin, a recombinant human insulin, an insulin from a non-human animal, a fast-acting insulin, an intermediate-acting insulin, a long-acting insulin, and combinations thereof; and
   (b) an insulin aptamer-glucagon conjugate comprising an insulin aptamer covalently conjugated to glucagon or to a bioactive derivative thereof, wherein said insulin aptamer is an oligonucleotide, and wherein said bioactive derivative retains at least some of the biological activity of endogenous glucagon;
wherein the insulin aptamer can selectively bind to the insulin or bioactive derivative thereof, thereby forming a non-covalent conjugate between (a) and (b).

2. The composition of claim 1, wherein the polymer is biodegradable.

3. The composition of claim 1, wherein the polymer is hyaluronic acid or a derivatized hyaluronic acid.

4. The composition of claim 1, wherein the polymer and the insulin or bioactive derivative thereof are covalently conjugated via an amide linkage.

5. The composition of claim 1, wherein the insulin is human recombinant insulin.

6. The composition of claim 1, wherein the glucagon is a thiolated glucagon, and the glucagon and the insulin aptamer are covalently conjugated via a linker.

7. The composition of claim 1, wherein the composition is cross-linked with a crosslinker to form a hydrogel matrix.

8. A pharmaceutical composition comprising a composition of claim 1 and a pharmaceutically acceptable carrier.

9. A microneedle array comprising a composition of claim 1, wherein said microneedle array comprises a plurality of microneedles, wherein each of said plurality of microneedles has a length of between about 20 and about 1000 microns.

10. A skin patch comprising a microneedle array of claim 9.

11. A closed-loop glucagon delivery system comprising a microneedle array of claim 9.

12. A method of delivering glucagon or a bioactive derivative thereof to a subject in need thereof, the method comprising providing a microneedle array of claim 11, and applying said array to a skin surface of said subject, thereby penetrating the skin surface with microneedles of the microneedle array to expose said microneedles to interstitial fluid, wherein the delivery of the glucagon or the bioactive derivative thereof is at a rate corresponding to the insulin concentration in the interstitial fluid coming into contact with the microneedles.

13. The method of claim 12, wherein the subject is a mammal.

14. The method of claim 12, wherein the subject is diabetic and/or is being treated for a disease or disorder with insulin replacement therapy, a sulfonylurea, or a meglitinide.

15. The method of claim 12, wherein the subject is non-diabetic and suffers from hyperinsulinemic hypoglycemia.

16. A method of preparing a microneedle array for the insulin-responsive delivery of glucagon or a bioactive derivative thereof, the method comprising:
   (a) providing a mold comprising one or more microcavities;
   (b) filling at least a portion of the one or more microcavities of the mold with a first solution comprising: (i) a composition of claim 1, (ii) a crosslinking agent; and (iii) a photoinitiator;
   (c) drying the filled mold to remove water;
   (d) removing the mold to provide a microneedle array; and
   (e) exposing the microneedle array to UV radiation to provide a crosslinked microneedle array.

17. The method of claim 16, wherein the mold comprises silicone.

18. The method of claim 16, further comprising filling a portion of the mold with a second solution comprising a biocompatible polymer, a crosslinking agent, and a photoinitiator.

19. The composition of claim 1, wherein the hydrophilic polymer is a synthetic block copolymer or a polysaccharide.

20. The composition of claim 19, wherein the hydrophilic polymer is a glucosaminoglycan.

21. The composition of claim 3, wherein the polymer is a methacrylated hyaluronic acid.

22. The composition of claim 1, wherein the oligonucleotide comprises the sequence of SEQ ID NO: 1 or SEQ ID NO: 4.

23. The composition of claim 6, wherein the linker is sulfosuccinimidyl-4-(N-maleimidomethyl)-cyclohexane-1-carboxylate (Sulfo-SMCC).

24. The composition of claim 7, wherein the crosslinker is N, N'-methylenebisacrylamide.

25. The microneedle array of claim 9, wherein each of the plurality of microneedles has a length of about 600 microns.

26. The skin patch of claim 10, wherein said skin patch comprises one or more backing layers and/or skin-compatible adhesives.

27. The method of claim 15, wherein the subject has a disease or disorder selected from the group consisting of congenital hyperinsulinism, an insulinoma, gastric dumping syndrome, autoimmune insulin syndrome, and reactive hypoglycemia.

28. The method of claim 16, wherein each of the one or more microcavities is approximately conical in shape and/or wherein the microcavities have a depth of between about 300 and about 900 micrometers.

29. The method of claim 18, wherein the biocompatible polymer is methacrylated hyaluronic acid.

* * * * *